(12) United States Patent
Budhabhatti et al.

(10) Patent No.: US 10,195,055 B2
(45) Date of Patent: Feb. 5, 2019

(54) ANTERIOR AND POSTERIOR REFERENCING SIZING GUIDES AND CUTTING BLOCKS AND METHODS

(71) Applicant: Smith & Nephew, Inc., Memphis, TN (US)

(72) Inventors: Sachin P. Budhabhatti, Collierville, TN (US); Ravi Bagathur Ramasamy, Collierville, TN (US); Tom J. Francis, Cordova, TN (US); Christopher Cyko, Memphis, TN (US)

(73) Assignee: Smith & Nephew, Inc., Memphis, TN (US)

( * ) Notice: Subject to any disclaimer, the term of this patent is extended or adjusted under 35 U.S.C. 154(b) by 50 days.

(21) Appl. No.: 15/117,974

(22) PCT Filed: Feb. 11, 2015

(86) PCT No.: PCT/US2015/015391
§ 371 (c)(1),
(2) Date: Aug. 10, 2016

(87) PCT Pub. No.: WO2015/123279
PCT Pub. Date: Aug. 20, 2015

(65) Prior Publication Data
US 2016/0361178 A1 Dec. 15, 2016

Related U.S. Application Data

(60) Provisional application No. 61/938,489, filed on Feb. 11, 2014, provisional application No. 61/938,504, filed on Feb. 11, 2014.

(51) Int. Cl.
*A61F 2/46* (2006.01)
*A61B 17/15* (2006.01)
(Continued)

(52) U.S. Cl.
CPC .......... *A61F 2/4657* (2013.01); *A61B 17/155* (2013.01); *A61B 17/1764* (2013.01); *A61B 2090/061* (2016.02); *A61F 2002/4658* (2013.01)

(58) Field of Classification Search
CPC ..... A61B 17/17; A61B 17/1764; A61B 17/15; A61B 17/155
See application file for complete search history.

(56) References Cited

U.S. PATENT DOCUMENTS

| | | | |
|---|---|---|---|
| 6,013,081 A | 1/2000 | Burkinshaw et al. | |
| 2005/0240195 A1* | 10/2005 | Axelson, Jr. ......... | A61B 17/155 606/87 |

(Continued)

FOREIGN PATENT DOCUMENTS

| | | |
|---|---|---|
| CL | 200202375 A | 11/2013 |
| CL | 201400438 A | 10/2014 |

(Continued)

OTHER PUBLICATIONS

International Search Report; European Patent Office; International Application No. PCT/US2015/015391; dated Jul. 3, 2015; 6 pages.
(Continued)

*Primary Examiner* — Christopher Beccia
(74) *Attorney, Agent, or Firm* — Taft Stettinius & Hollister LLP

(57) ABSTRACT

Embodiments of the invention include instruments and methods for preparing a femur to receive a femoral component of a knee arthroplasty system, with some embodiments configured to enable anterior referencing techniques, posterior referencing techniques, and to facilitate intraoperative switching between anterior and posterior referencing techniques. Other embodiments of the invention include cutting blocks and methods for preparing a femur to receive a knee arthroplasty system femoral component, with some embodi- (Continued)

ments including cutting blocks that can be used in both an anterior referencing technique and a posterior referencing technique, thereby reducing the number of cutting blocks required to provide an instrument set capable of implanting all available sizes of femoral components with both anterior and posterior referencing techniques.

28 Claims, 9 Drawing Sheets

(51) Int. Cl.
*A61B 17/17* (2006.01)
*A61B 90/00* (2016.01)

(56) References Cited

U.S. PATENT DOCUMENTS

2006/0142778 A1 6/2006 Dees
2010/0324563 A1 12/2010 Green, II et al.
2013/0144302 A1* 6/2013 Reeve ............... A61B 17/155
 606/102
2015/0032114 A1 1/2015 Dmuschewsky

FOREIGN PATENT DOCUMENTS

CL 201400094 A 11/2014
WO 2013026926 A1 2/2013

OTHER PUBLICATIONS

Written Opinion of the International Searching Authority; European Patent Office; International Application No. PCT/US2015/015391; dated Jul. 3, 2015; 9 pages.
Chinese Office Action (1st); State Intellectual Property Office, Peoples Republic of China; Chinese Patent Application No. 201580019320.4; dated Jun. 5, 2018; 11 pages.
European Examination Report, European Patent Office, European Patent Application No. 15706344.7, dated May 9, 2018, 6 pages.
Chiliean Office Action; Chilean Patent Office; Chilean Patent Application No. 2016-02015; dated Jul. 12, 2018; 11 pages.

* cited by examiner

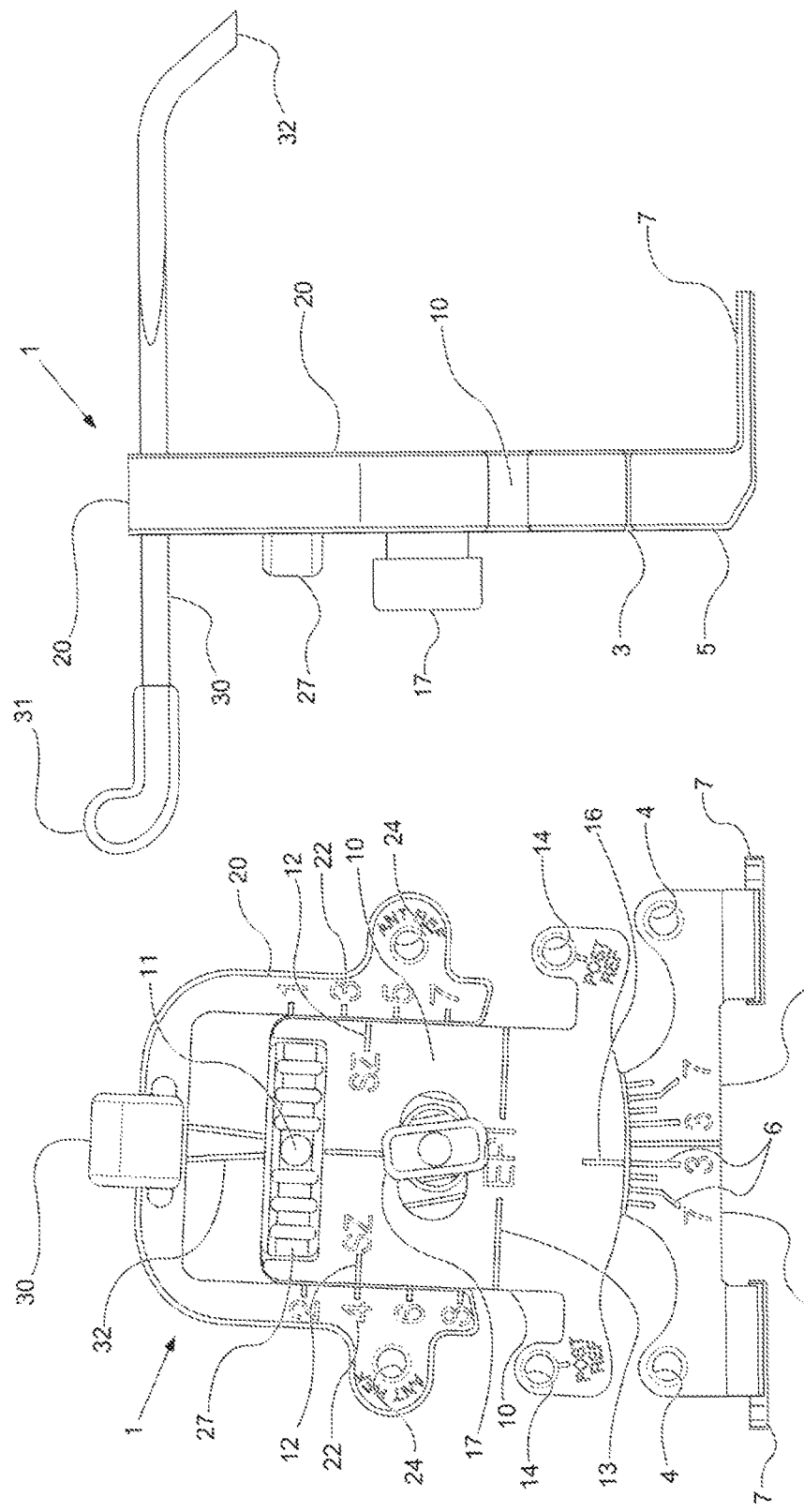

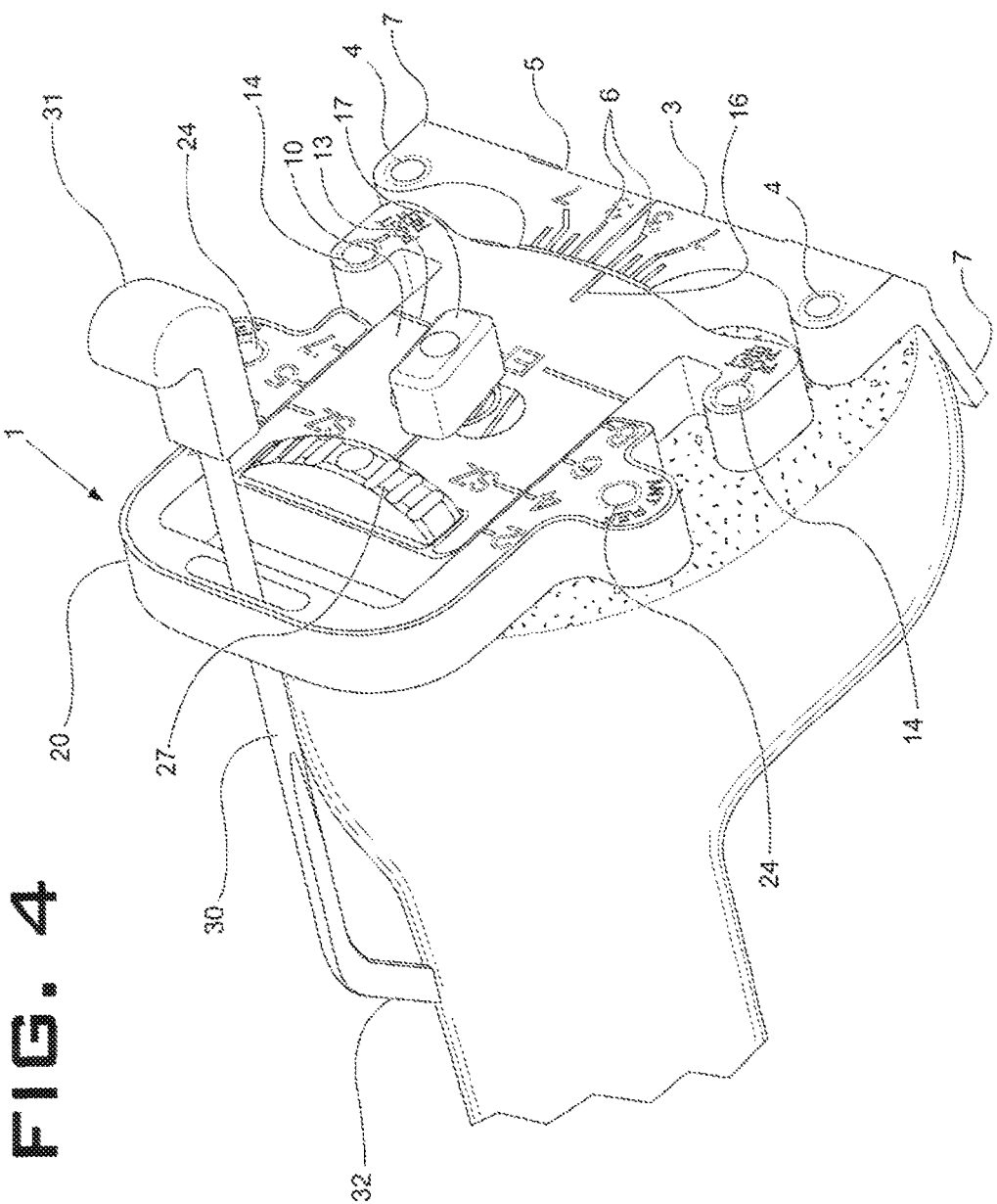

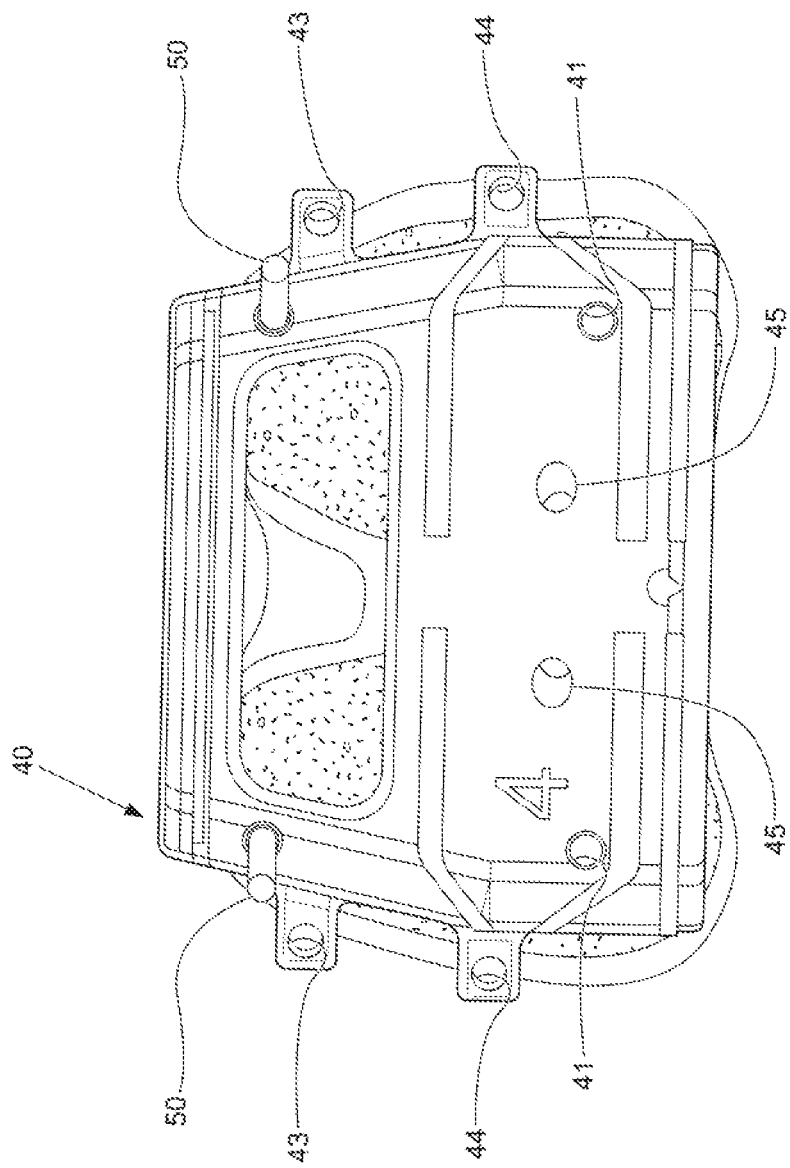

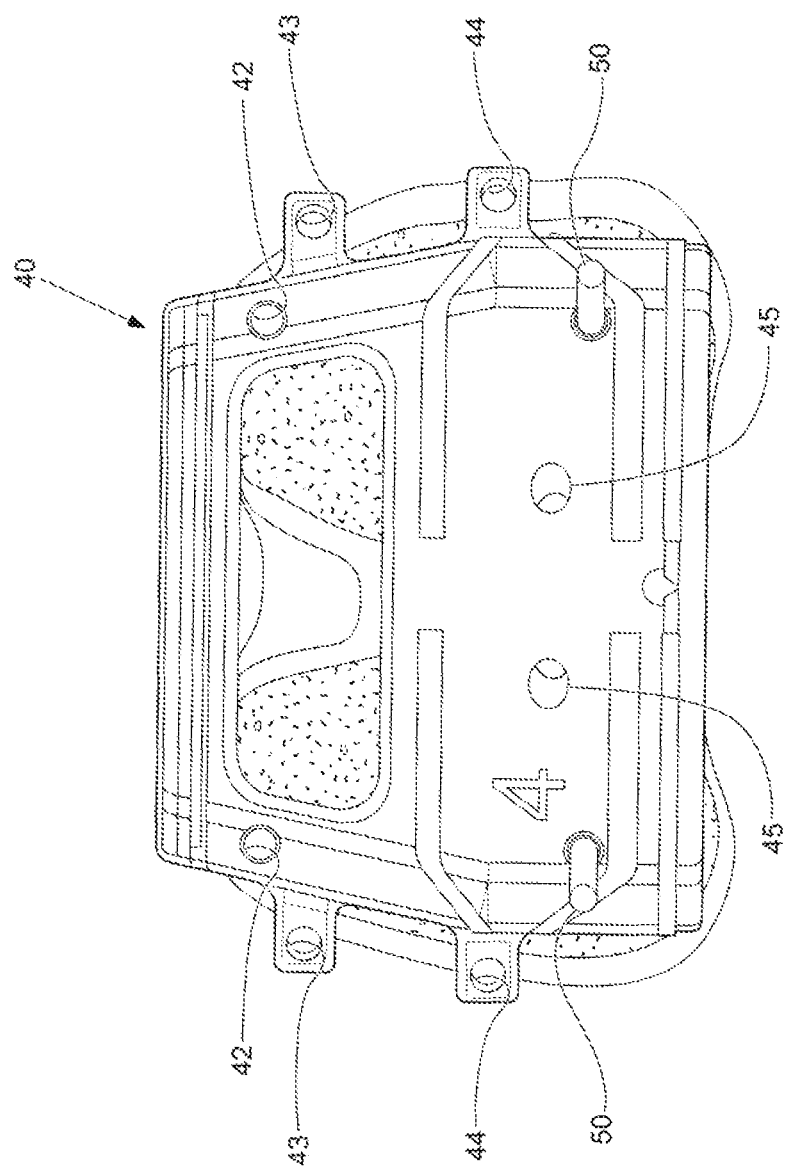

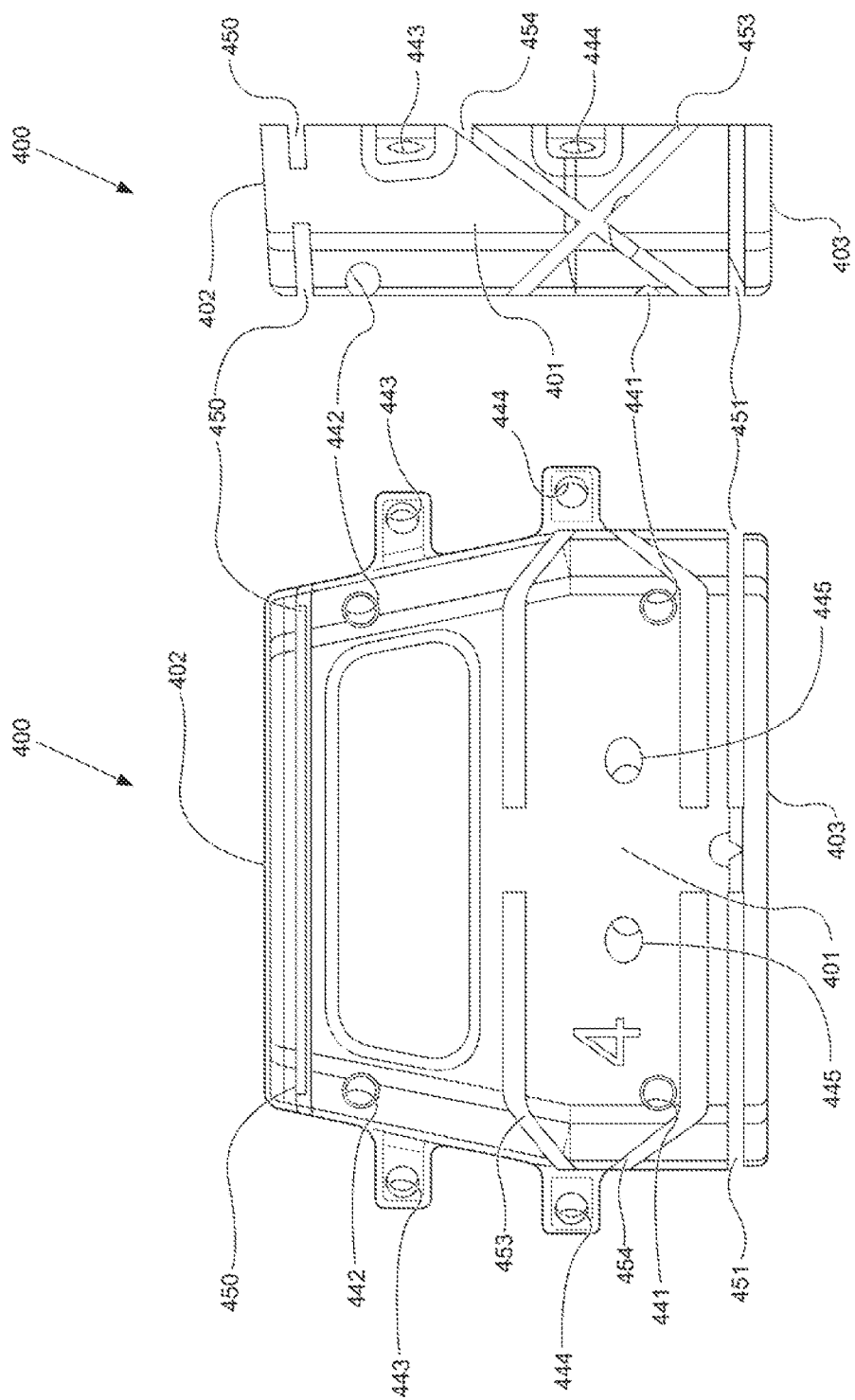

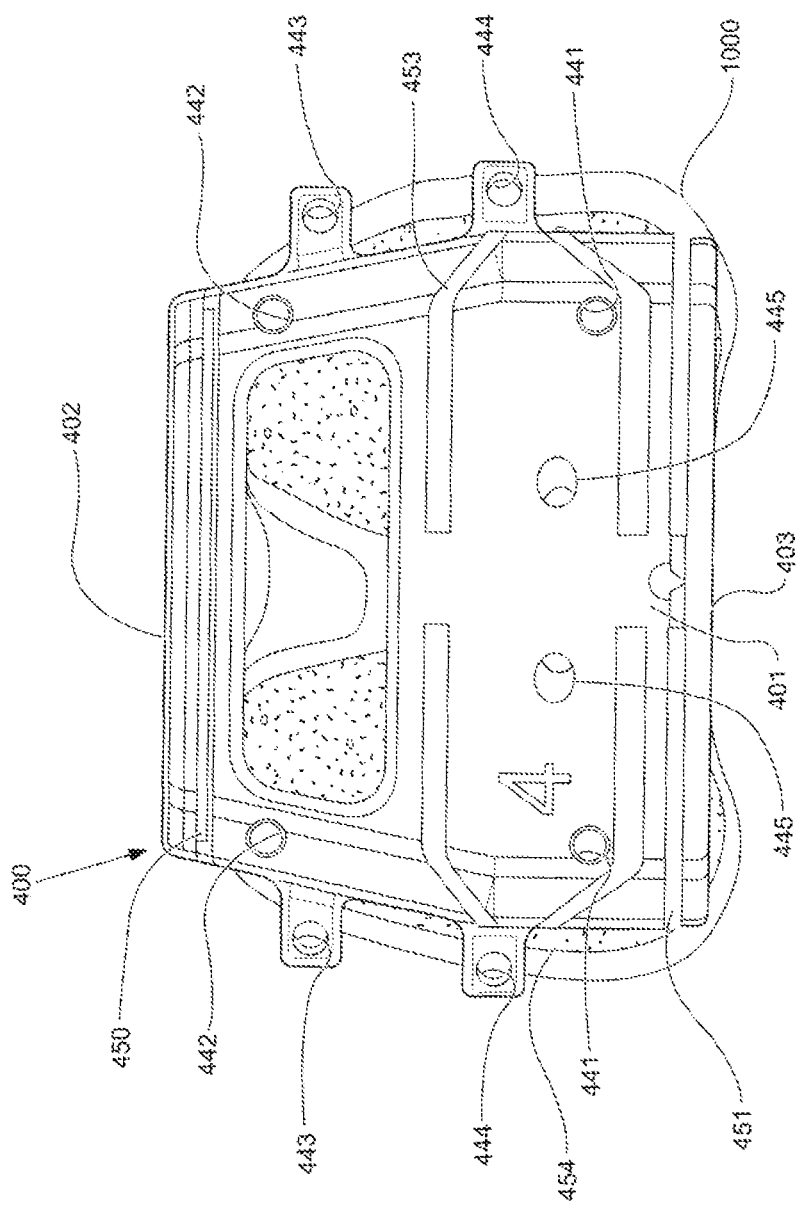

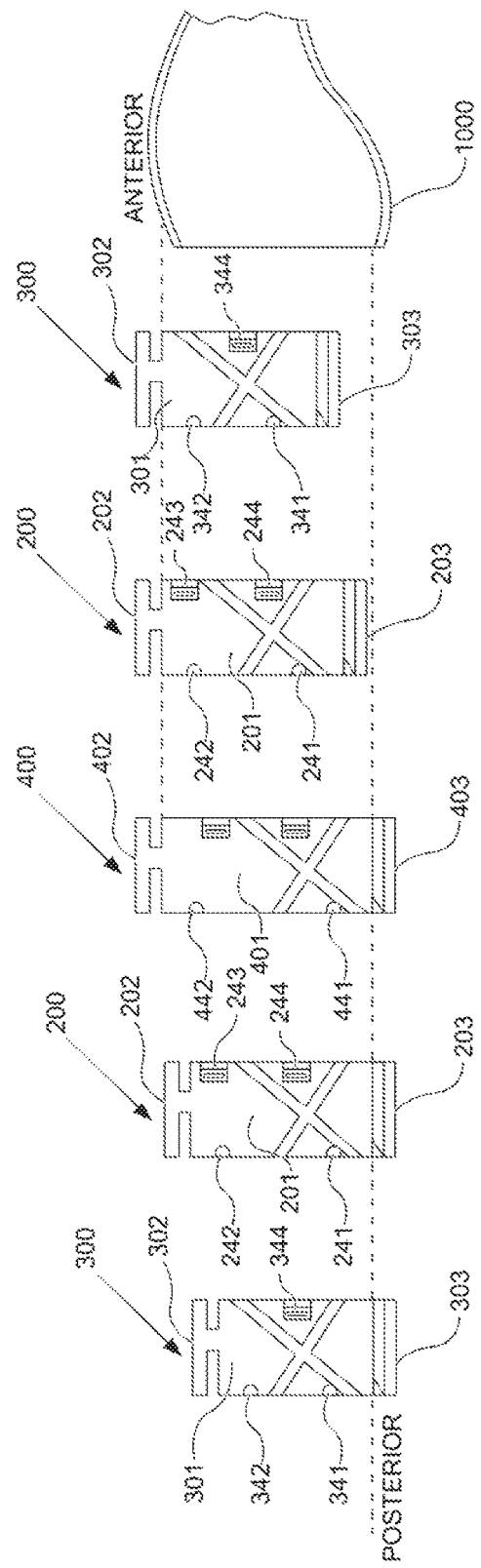

ANTERIOR AND POSTERIOR REFERENCING SIZING GUIDES AND CUTTING BLOCKS AND METHODS

CROSS REFERENCE TO RELATED APPLICATIONS

This application is a U.S. National Phase of International PCT Application No. PCT/US2015/015391 filed Feb. 11, 2015, which claims the benefit of U.S. Provisional Application No. 61/938,489 filed Feb. 11, 2014 and U.S. Provisional Application No. 61/938,504 filed Feb. 11, 2014, the contents of each application hereby incorporated by reference in their entirety.

FIELD OF THE INVENTION

The present invention relates generally to the field of medical instruments, and more particularly relates to instruments and methods for aligning a guide for cutting a femur to receive a femoral component of a knee arthroplasty system, and instruments and methods for cutting femur to receive a femoral component of a knee arthroplasty system.

BACKGROUND

Current knee arthroplasty systems require specialized instruments of many varieties for the purposes of, for example, treating left and right knees, referencing either the anterior or posterior portion of a femur to align an implant, accommodating many different sizes, and matching many different degrees of external rotation. Various combinations of instruments purposed in these many different ways can lead to very large sets of instruments required to accomplish even the one basic task of aligning a femoral component on a patient's femur. Additionally, femoral cutting blocks used in many current knee arthroplasty systems are typically provided in multiple varieties and sizes. Providing cutting blocks of multiple varieties and sizes can contribute significantly to the bulk of current knee arthroplasty systems because cutting blocks are typically relatively heavy and can be very numerous in cases where an instrument set is designed to support implantation of a large number of sizes of knee arthroplasty components. As should be appreciated, large instrument sets are expensive to manufacture, expensive to ship, cumbersome to handle, time and cost intensive to clean and sterilize, and may be more complicated to learn to use effectively.

A single instrument or reduced number of instruments and related techniques designed and configured to accomplish multiple ones of the above-discussed purposes could therefore reduce costs, improve efficiency, and improve overall results. Such a single instrument or reduced number of instruments may also reduce or eliminate the need to change instruments intraoperatively.

In instances where a surgeon would like to switch between an anterior referencing technique and a posterior referencing technique intraoperatively, a single instrument with features applicable and valuable to each technique would be beneficial. An anterior referencing technique makes primary spatial reference to the anterior cortex of a patient's femur, and anterior resection is fixed while posterior resection varies with implant size. Because a femoral component is typically positioned generally flush against the anterior cortex, an anterior referencing technique enables reapproximation of the patellofemoral joint. An anterior referencing technique also reduces the chance of notching the anterior cortex of a patient's femur. One disadvantage associated with an anterior referencing technique is that such techniques may tend to lead to a patient's treated knee being loose in flexion. A posterior referencing technique makes primary spatial reference to a patient's posterior femoral condyles, and posterior resection remains constant while anterior resection varies with respect to the anterior cortex of the femur. Therefore, the posterior resection will equal the posterior thickness of the prosthesis, thereby resulting in a balanced flexion-extension space. One disadvantage associated with a posterior referencing technique is that such techniques may lead to overstuffing of the patellofemoral joint and notching of the anterior cortex of the femur.

In cases where a surgeon would like to intraoperatively reduce the size of the femoral component being used for one or more reasons, and a posterior referencing technique is being used, a better clinical result may sometimes be achieved by switching from a posterior referencing technique to an anterior referencing technique. Such implant downsizing accomplished during a posterior referencing technique alone is very likely to lead to notching of the anterior cortex of the femur. An improved instrument or instrument set and related techniques may provide a surgeon with the option of transitioning from a posterior referencing technique to an anterior referencing technique with little or no change to the associated instrumentation.

Additionally, current knee arthroplasty systems include separate cutting blocks for use with anterior referencing techniques and posterior referencing techniques. Cutting blocks having multiple applications associated with various uses of a knee arthroplasty instrument set would reduce the number of instruments in the instrument set, and would therefore address some of the limitations of currently available instrument sets. For example, cutting blocks that may be used in both anterior and posterior referencing techniques have the potential to significantly reduce the number of cutting blocks required in an instrument set.

SUMMARY

An embodiment of the invention is directed to a femoral sizing guide having a base that includes a main body and one or more paddles that extend from the main body, wherein the one or more paddles are configured to contact posterior condyles of a patient. The femoral sizing guide may also include a posterior reference frame pivotally coupled with the base, wherein the posterior reference frame includes one or more holes for receiving one or more fasteners, an anterior reference frame slidably coupled to the posterior reference frame, and a stylus coupled to the anterior reference frame. The stylus may extend away from the plane in which the anterior reference frame slides relative to the posterior reference frame.

Another embodiment of the invention is directed to a method of preparing a femur to receive a femoral component of a knee arthroplasty system. The method may include making a distal cut across the femur and placing a femoral sizing guide against the distal cut. Femoral sizing guide embodiments include a base having a main body and one or more paddles that extend from the main body, wherein the one or more paddles are configured to contact posterior condyles of the femur, a posterior reference frame coupled with the base, an anterior reference frame slidably coupled to the posterior reference frame, and a stylus coupled to the anterior reference frame. The stylus may extend away from the plane in which the anterior reference frame slides relative to the posterior reference frame. The method may further include seating the one or more paddles against the posterior condyles of the femur, sliding the anterior reference frame relative to the posterior reference frame and adjusting the stylus to contact the lateral anterior cortex of the femur, and determining a size of femoral component to implant based on indications displayed on the femoral sizing guide. In some embodiments, an option is provided to place both fasteners through one or more holes in the posterior reference frame and/or through one or more holes in the anterior reference frame, wherein placing fasteners through one or more holes in the posterior reference frame facilitates a posterior referencing technique, and wherein placing fasteners through one or more holes in the anterior reference frame facilitates an anterior referencing technique. The method may further include removing the femoral sizing guide from the femur and coupling a cutting block to the femur by alignment with one or more of the fasteners.

Yet another embodiment of the invention is directed to a method of preparing a femur to receive a femoral component of a knee arthroplasty system. The method may include making a distal cut across the femur and placing a femoral sizing guide against the distal cut. The femoral sizing guide may have a base that includes a main body and one or more paddles that extend from the main body. The one or more paddles may be configured to contact posterior condyles of the femur. The femoral sizing guide may also include a posterior reference frame coupled with the base, an anterior reference frame slidably coupled to the posterior reference frame, and a stylus coupled to the anterior reference frame, wherein the stylus extends away from the plane in which the anterior reference frame slides relative to the posterior reference frame. The method embodiment may also include seating the one or more paddles against the posterior condyles of the femur, sliding the anterior reference frame relative to the posterior reference frame and adjusting the stylus to contact the lateral anterior cortex of the femur, and determining a size of femoral component to implant based on indications displayed on the femoral sizing guide. Some method embodiments include the option to place fasteners through one or more holes in the posterior reference frame and/or through one or more holes in the anterior reference frame, wherein placing fasteners through one or more holes in the posterior reference frame facilitates a posterior referencing technique, and wherein placing fasteners through one or more holes in the anterior reference frame facilitates an anterior referencing technique. Method embodiments may further include placing fasteners through the one or more holes in the posterior reference frame while performing a posterior referencing technique, selecting a femoral component of a smaller size than initially determined, changing to an anterior referencing technique, placing fasteners through the one or more holes in the anterior reference frame, and removing the femoral sizing guide from the femur and coupling an anterior referencing cutting block to the femur with one or more of the fasteners placed through the one or more holes in the anterior reference frame.

Yet another embodiment of the invention is directed to a cutting block having a body that includes two or more slots configured to receive and direct a cutting instrument used to prepare a distal femur to receive a femoral component of a knee arthroplasty system. The cutting block may also include one or more anterior holes in the anterior half of the body that are configured to align with one or more fasteners placed in the femur after being aligned by a guide used to reference an anterior portion of the femur, and one or more posterior holes in the posterior half of the body that are configured to align with one or more fasteners placed in the femur after being aligned by a guide used to reference a posterior portion of the femur.

Yet another embodiment of the invention is directed to a kit of cutting blocks. A first cutting block may have a body that includes two or more slots configured to receive and direct a cutting instrument used to prepare a distal femur to receive a femoral component of a knee arthroplasty system, one or more anterior holes in the anterior half of the body that are configured to align with one or more fasteners placed in the femur after being aligned by a guide used to reference an anterior portion of the femur, and one or more posterior holes in the posterior half of the body that are configured to align with one or more fasteners placed in the femur after being aligned by a guide used to reference a posterior portion of the femur. The kit may also include a second cutting block of a smaller size than the first cutting block. The second cutting block may also have one or more anterior holes that are substantially the same anterior to posterior distance from the anterior side of the second cutting block as the one or more anterior holes of the first cutting block are from the anterior side of the first cutting block, and one or more posterior holes that are substantially the same anterior to posterior distance from the posterior side of the second cutting block as the one or more posterior holes of the first cutting block are from the posterior side of the first cutting block.

Still another embodiment of the invention is directed to a method of implanting a knee arthroplasty femoral component. Such method embodiments may provide a first cutting block of a particular size and a second cutting block of a size smaller than the size of the first cutting block, wherein the second cutting block is configured to either be aligned with an anterior reference to a femur or a posterior reference to the femur. Method embodiments may further include choosing to downsize to the size of the second cutting block intraoperatively, aligning the second cutting block with either an anterior reference or a posterior reference, cutting the femur as guided by the cutting block, and implanting the knee arthroplasty femoral component.

BRIEF DESCRIPTION OF THE DRAWINGS

FIG. 2 is an elevation view of the femoral sizing guide of FIG. 1 in an expanded state.

FIG. 3 is a side elevation view of the femoral sizing guide of FIG. 2.

FIG. 4 is a perspective view of the femoral sizing guide of FIG. 2 positioned relative to a resected femur.

FIG. 6 is an elevation view of an embodiment of a 4-in-1 cutting block positioned relative to a resected femur and pinned with anterior fasteners.

FIG. 7 is an elevation view of the 4-in-1 cutting block of FIG. 6 positioned relative to a resected femur and pinned with posterior fasteners.

FIG. 8 is an elevation view of an embodiment of a cutting block.

FIG. 9 is a medial to lateral side elevation view of the cutting block of FIG. 8.

FIG. 10 is an elevation view of the cutting block of FIG. 8 positioned relative to a resected femur.

FIG. 11 is a medial to lateral side elevation view of multiple cutting blocks positioned in anterior to posterior alignment relative to a distal end of a resected femur.

DETAILED DESCRIPTION

Figure 1:
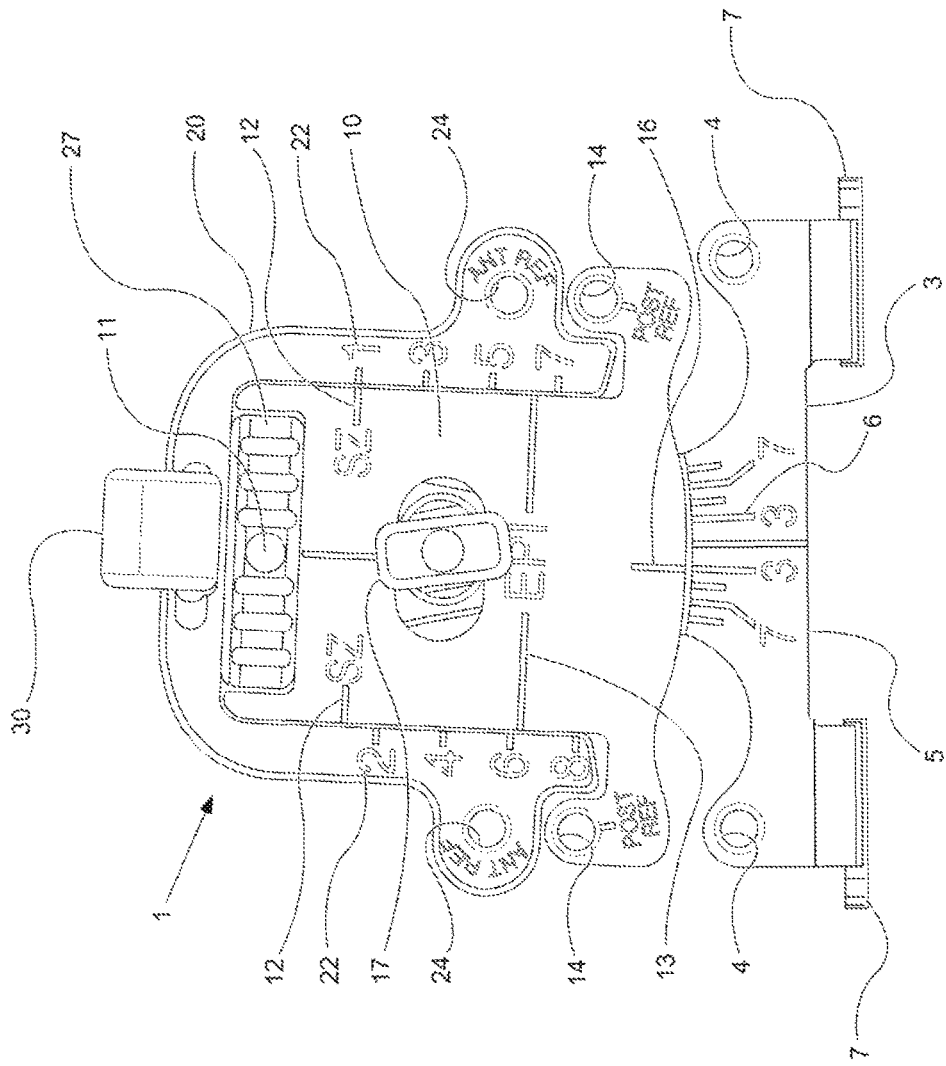
FIG. 1 is an elevation view of an embodiment of a femoral sizing guide.
Figure 5:
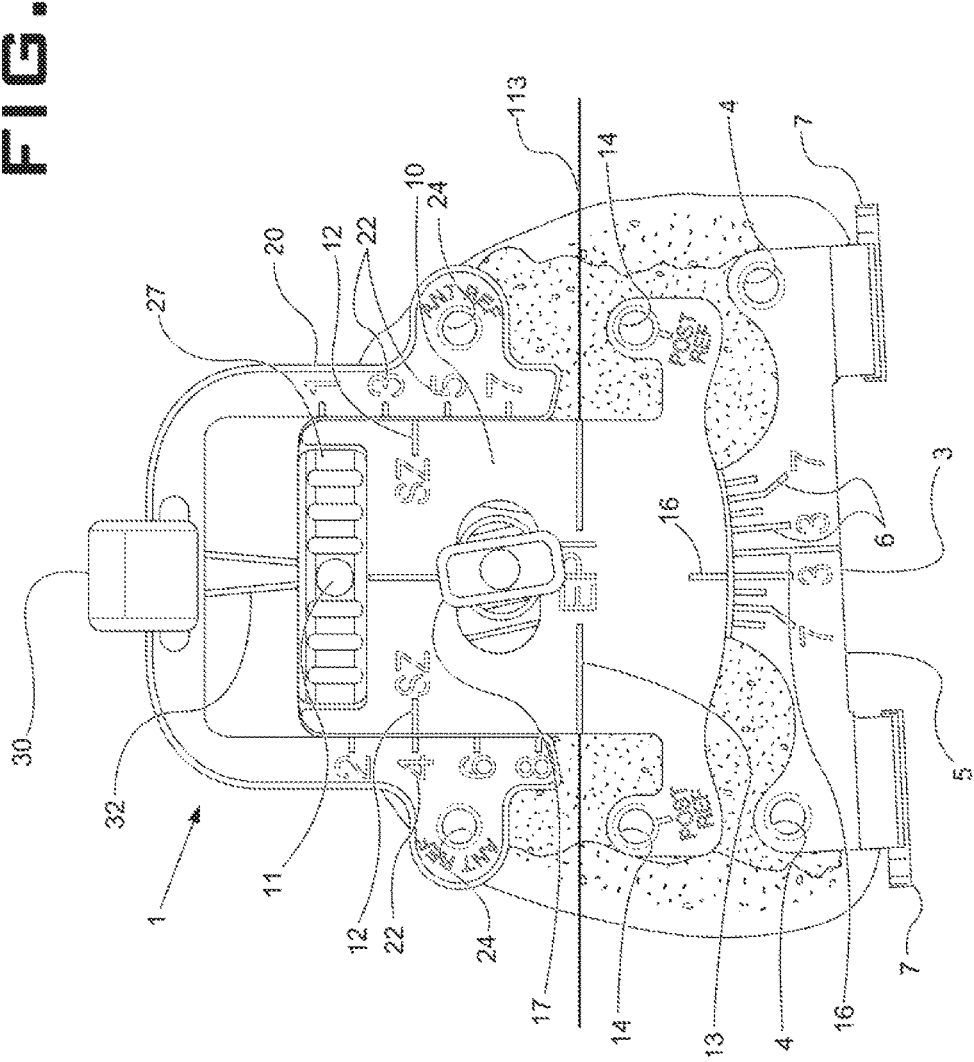
FIG. 5 is an elevation view of the femoral sizing guide of FIG. 2 shown in place on a resected femur.

Referring to FIGS. 1-5, shown therein is an embodiment of a femoral sizing guide 1 which generally includes a base 3 having a main body 5 and two paddles 7 that extend from the main body 5. In the illustrated embodiment, the paddles 7 are configured to contact posterior condyles of a patient (FIGS. 4 and 5). However, other embodiments of a base may contact the patient's femur at other locations and/or with other types of mechanisms. The illustrated base 3 includes two base holes 4 for receiving one or more fasteners. Examples of suitable fasteners include but are not limited to pins, screws, dowels, rods, spikes, or any other suitable or effective mechanism that may be attached or anchored to bone. Such fasteners may be configured with or without heads or similar mechanisms that may be used to hold or otherwise engage a base against a femur or another bone.

In the illustrated embodiment, a posterior reference frame 10 is pivotally coupled with the base 3 at a pivot 11. The illustrated posterior reference frame 10 also includes two holes 14 for receiving fasteners. Other embodiments may include a greater or lesser number of holes for receiving fasteners. Examples of suitable fasteners include but are not limited to pins, screws, dowels, rods, spikes, or any other suitable or effective mechanism that may be attached or anchored to bone, and may or may not include a head or similar mechanism. In some embodiments, none of the holes for receiving fasteners are configured to receive an intramedullary rod. A configuration to receive an intramedullary rod may be unnecessary in embodiments that do not include the use of an intramedullary rod, or where a designed procedure dictates removal of an intramedullary rod prior to use of a femoral sizing guide. The pivot 11 between the base 3 and the posterior reference frame 10 is in the anterior quarter portion of the posterior reference frame 10. Pivot points of various embodiments may be located further posterior relative to posterior reference frames of various embodiments. For example and without limitation, a pivot between a base and a posterior reference frame may be positioned within the anterior half of the posterior reference frame. By way of further example and without limitation, a pivot between a base and a posterior reference frame may be positioned within the anterior third of the posterior reference frame.

The femoral sizing guide 1 includes a posterior lock 17 (FIGS. 1-5) configured to restrict pivoting of the posterior reference frame 10 relative to the base 3. The illustrated posterior lock 17 is threadedly engaged with the base 3 (or with a nut integrated with or behind the base 3) and compresses the posterior reference frame 10 with the base 3 when actuated, thereby restricting pivoting of the posterior reference frame 10 relative to the base 3. Other embodiments may include a posterior lock of any type that suitably and effectively restricts pivoting between a posterior reference frame and a base. Posterior locks of various embodiments may also restrict other relative movements in addition to pivoting. The posterior reference frame 10 illustrated in FIGS. 1-5 also includes an indicator 16 configured to be read relative to the indicator's position on a scale 6 associated with the base 3. The indicator 16 and the scale 6 in combination show degrees of external rotation, either clockwise or counterclockwise, that may be recorded and acted upon when sizing a particular patient's femoral condyles relative to the patient's epicondylar axis. In other embodiments, an indicator and scale can take any suitable or effective form, and may be provided in any suitable or effective configuration. For example and without limitation, an indicator may be included on a base configured to be read relative to the indicator's position on a scale on a posterior reference frame.

The femoral sizing guide 1 illustrated in FIGS. 1-5 also includes an anterior reference frame 20 slidably coupled to the posterior reference frame 10. The illustrated anterior reference frame 20 includes two holes 24 for receiving two fasteners. Other embodiments may include a greater or lesser number of holes for receiving fasteners. Examples of suitable fasteners include but are not limited to pins, screws, dowels, rods, spikes, or any other suitable or effective mechanism that may be attached or anchored to bone, and may or may not include a head or similar mechanism. In some embodiments, the one or more holes for receiving one or more fasteners in the posterior reference frame and the one or more holes for receiving one or more fasteners in the anterior reference frame are different such that an instrument configured to couple with fasteners aligned for use with the posterior reference frame will not couple with fasteners aligned for use with the anterior reference frame. By way of example and without limitation, the one or more holes in the posterior reference frame may be one or more of a different pitch, a different size, and/or provided in a different pattern relative to the one or more holes in the anterior reference frame. Such a configuration may prevent fasteners placed in the posterior reference frame to facilitate a posterior referencing technique from inadvertently being used in association with an instrument configured for use in an anterior referencing technique, or vice versa. By way of a specific example and without limitation, if the two holes 14 in the posterior reference frame 10 are a separated by a different medial-to-lateral distance than the two holes 24 in the anterior reference frame 20, then an instrument, such as a cutting block, intended for use in a posterior referencing technique would not fit fasteners correspondingly placed for an anterior referencing technique via the holes 24.

The illustrated posterior reference frame 10 includes size indicia 12 configured to work in conjunction with a sizing scales 22 on the anterior reference frame 20. The size indicia 12 shown are at the same anterior to posterior dimension. The illustrated sizing scales 22 include odd sizes on the right-hand side and even sizes on the left-hand side. This configuration allows space for larger sized numerals to be printed on the anterior reference frame 20. Other embodiments may include reversal of the size indicia and scales, may not necessarily include scales contralaterally located relative to one another, and may in general include any suitable or effective mechanism for indicating relative sliding between a posterior reference frame and an anterior reference frame.

One embodiment of an anterior lock 27 is illustrated in FIGS. 1-5. The anterior lock 27 is configured to restrict sliding of the anterior reference frame 20 relative to the posterior reference frame 10 when actuated. The illustrated anterior lock 27 is configured as a thumbwheel that when turned in one direction moves other mechanisms (not shown to restrict sliding of the anterior reference frame 20 relative to the posterior reference frame 10. When turned in an opposite direction, the mechanisms are released to allow for sliding of the anterior reference frame 20 relative to the posterior reference frame 10. Any other suitable or effective configuration that selectively restricts sliding between an anterior reference frame and a posterior reference frame may also be used as an anterior lock.

One embodiment of a stylus 30 is illustrated in FIGS. 1-5. The illustrated stylus 30 is coupled to the anterior reference frame 20 and extends away from the plane in which the anterior reference frame 20 slides relative to the posterior reference frame 10. As illustrated in FIGS. 3 and 4, the stylus 30 includes a control end 31 and a measurement end 32. The control end 31 may be gripped by a user for moving the stylus 30 relative to the anterior reference frame 20. The distance from the control end 31 to the anterior reference frame 20 may also be used as an indicator to indicated a proper length and placement of the stylus 30. The measurement end 32 is configured to contact a portion of a patient's femur, and to gauge and/or position a femoral sizing guide. In the illustrated embodiment, the measurement end 32 is configured to contact the lateral anterior cortex of a patient's femur to assist with positioning the femoral sizing guide (FIG. 4).

One embodiment of a cutting block 40 is illustrated in FIGS. 6 and 7. The illustrated cutting block 40 is a modification of a standard 4-in-1 cutting block having slots for cutting anterior, posterior, and two chamfered cuts, as are well-known in the art. A similar cutting block and other variations of cutting blocks and related methods are set forth below. The illustrated cutting block 40 includes two posterior holes 41 (FIG. 6) and two anterior holes 42 (FIG. 7). Fasteners 50 are shown positioned in the anterior holes 42 (FIG. 6) and in the posterior holes 41 (FIG. 7). The anterior holes 42 are configured to align with fasteners that have been coupled with the femur through the two holes 24 in the anterior reference frame 20. The posterior holes 41 are configured to align with fasteners that have been coupled with the femur through the two holes 14 in the posterior reference frame 10. The cutting block 40 also includes several additional fastener holes 43, 44, 45 that may be used to couple the cutting block 40 to the femur at various times during procedures performed with the cutting block 40. For example, fasteners may be removed from select holes when the fasteners would interfere, with a cutting instrument during a particular step of a procedure, but positioned through select holes at another step of a procedure.

Once embodiment of the invention is directed to a method of preparing a femur to receive a femoral component of a knee arthroplasty system. An act or step of such an embodiment includes making a distal cut across a femur. The femur shown in FIGS. 4-7 has been distally cut. Another act or step associated with some embodiments includes placing a femoral sizing guide against the distal cut, as shown, for example, in FIGS. 4 and 5 where the femoral sizing guide 1 has been placed against the distal cut. The base 3 of the femoral sizing guide 1 may also be coupled to the femur through one or more holes, such as the holes 4 shown in FIGS. 1, 2, 4 and 5. This coupling may be accomplished at any operable time during the method. Femoral sizing guides used in such methods may be any variety of femoral sizing guide or their component parts that have been described above in relation to the femoral sizing guide and any other functionally similar device or mechanism. In particular, placing a femoral sizing guide may include placing a femoral sizing guide including at least a base with a main body and one or more paddies that extend from the main body, and wherein the one or more paddles are configured to contact posterior condyles of the femur.

As described in further detail herein, a femoral sizing guide may include a posterior reference frame coupled with the base, an anterior reference frame slidably coupled to the posterior reference frame, and a stylus coupled to the anterior reference frame, and wherein the stylus extends away from the plane in which the anterior reference frame slides relative to the posterior reference frame. Some embodiments include the act or step of seating the one or more paddles 7 against the posterior condyles of the femur, as shown in FIGS. 4 and 5. The act or step of placing a femoral sizing guide against the distal cut may also include placing a posterior reference frame that is pivotally coupled with the base against the distal cut. For example and without limitation, the posterior reference frame 10 is pivotally coupled with the base 3. In some embodiments, the posterior reference frame 10 is pivoted relative to the base 3 such that a line 13 (FIGS. 1, 2, 4 and 5) arranged substantially perpendicular to the anterior-to-posterior dimension of the posterior reference frame 10 is aligned with an epicondylar axis 113 (FIG. 5) of the femur, while the one or more paddles 7 are in contact with the posterior condyles of the femur. The posterior lock 17 may be activated to restrict pivoting of the posterior reference frame 10 relative to the base 3.

Positioning and determining the size of a cutting block to be used in the method illustrated in FIGS. 1-7 may also include sliding the anterior reference frame 20 relative to the posterior reference frame 10 and adjusting the stylus 30 to contact the lateral anterior cortex of the femur. By this combination of actions or steps, the stylus 30 is used to establish a maximum posterior depth of cut to be cut through the cutting block 40 anterior slot. With the femoral sizing guide aligned posteriorly and restrained in any suitable or effective manner, the appropriate size of cutting block and femoral component can be determined via the indication displayed on the size indicia 12 and the sizing scales 22. In the embodiment shown in FIGS. 2-5, the size indicia 12 aligns with the number "4" on the sizing scale 22 of the anterior reference frame 20. This indication determines that a size 4 cutting block and femoral implant should be used as a result of the accomplished sizing.

Additionally, the illustrated embodiment provides the option to place fasteners through one or more holes 14 in the posterior reference frame 10 and/or through one or more holes 24 in the anterior reference frame 20. Placing fasteners through one or more holes in the posterior reference frame facilitates a posterior referencing technique since the positioning of the posterior reference frame 10 is set based on the positioning of the base 3 and the paddles 7, which in turn contact against the posterior condyles. Placing fasteners through one or more holes in the anterior reference frame 20 facilitates an anterior referencing technique since the positioning of the anterior reference frame 20 is set based on the positioning of the stylus 30, which in turn contact against the anterior cortex of the femur. With the femoral sizing guide 1 appropriately positioned, fasteners may be placed both through one or more of the holes 14 in the posterior reference frame 10 and the holes 24 in the anterior reference frame 20.

As shown in FIGS. 6 and 7, the illustrated embodiment includes removing the femoral sizing guide 1 from the femur and coupling the cutting block 40 to the femur via alignment with one or more fasteners 50. As shown in FIG. 6, fasteners 50 placed through holes 24 in the anterior reference frame 20 may be used to couple the cutting block 40 to the femur. As shown in FIG. 7, fasteners 50 placed through holes 14 in the posterior reference frame 10 may be used to couple the cutting block 40 to the femur, in the illustrated embodiment, it should be noted that fasteners could have been placed through all of the holes 14, 24 since the measured size is exactly a size 4, and each of the fasteners would align with a posterior hole 41 and an anterior hole 42. Scenarios where a femoral sizing guide measured size does not exactly match a cutting block and implant size are addressed by some of the disclosed embodiments.

In some circumstances, the size of cutting block and femoral component determined via the indication displayed on the size indicia 12 and the sizing scales 22 falls between two discrete sizes. When this occurs, and sometimes for other reasons, a size larger or smaller than the measured size may be chosen. When using an anterior referencing technique and the sizing guide indicates a size between two discrete sizes, the smaller size is often selected. Choosing the smaller size results in more bone resection from the posterior condyles, which may result in increasing the flexion space, but anterior femoral notching is avoided. When using a posterior referencing technique and the sizing guide indicates a size between two discrete sizes, the larger size is often selected. This does, however, increase the chance of overstuffing the patellofemoral joint. In some embodiments, this situation may be addressed by unique features which allow changing from a posterior referencing technique to an anterior referencing technique intraoperatively, and selecting a femoral component of a smaller size.

An embodiment substantially similar to the method embodiment described via the act or step of providing an option to place fasteners through holes in the posterior and/or anterior reference frames is describe herein. Such an embodiment may include, for example, placing fasteners through the one or more holes 14 in the posterior reference frame 10 while performing a posterior referencing technique. In such an embodiment, a femoral component of a smaller size than initially determined may be selected intraoperatively or otherwise. This selection may be driven by the factors outlined above, or may result merely from a surgeon's choice or other factors, in some embodiments, the choice to downsize the implant may be accompanied by a decision to change from a posterior referencing technique to an anterior referencing technique. Fasteners 50 intended for posterior holes 41 may be removed in embodiments where an anterior referencing technique is going to be pursued. To continue with an anterior referencing technique, fasteners 50 may be placed through holes 24 in the anterior reference frame 20.

As shown in FIG. 6, an anterior referencing technique may include removing the femoral sizing guide 1 from the femur and coupling the cutting block 40 to the femur by alignment with the fasteners 50 that were previously placed through holes 24 in the anterior reference frame 20. With the cutting block 40 appropriately placed, accurate cuts to the femur may be made followed by implantation of the knee arthroplasty components.

One embodiment of a cutting block 400 is illustrated in FIGS. 8-11. The illustrated cutting block 400 is a modification of a standard 4-in-1 cutting block having slots for cutting anterior, posterior, and two chamfered cuts, as are 1-1well-known in the art. Specifically, the cutting block 400 includes a body 401, an anterior slot 450, a posterior slot 451, and two intersecting slots, and more specifically an anterior-to-posterior slot 453 and a posterior-to-anterior slot 454, each configured to receive and direct a cutting instrument used to prepare a distal femur to receive a femoral component of a knee arthroplasty system. Other embodiments of a cutting block may include a greater or lesser number of slots or other mechanisms for directing the cutting or shaping of a femur.

The illustrated cutting block 400 includes two posterior holes 441 and two anterior holes 442. The two anterior holes 442 are positioned in the anterior half of the body 401 and are configured to align with one or more fasteners placed in a femur, such as the femur 1000 shown in FIGS. 10 and 11, after being aligned using a guide to reference an anterior portion of the femur 1000. The two anterior holes 442 are also positioned within the anterior quarter of the body 401, and are each positioned substantially the same anterior-to-posterior distance away from an anterior side 402 of the body 401. However, in other embodiments, the anterior holes 442 may be positioned different distances away from the anterior side 402. The anterior holes may also be of various sizes and shapes, and may include more or less than two holes. The illustrated cutting block 400 also includes posterior holes 441 in the posterior half of the body 401 that are configured to align with fasteners that have been placed in the femur 1000 after being aligned by a guide used to reference a posterior portion of the femur 1000. The two posterior holes 441 are also positioned within the posterior quarter of the body 401. The two posterior holes 441 are each positioned substantially the same anterior-to-posterior distance away from a posterior side 403 of the body 401. However, in other embodiments, the posterior holes 441 may be positioned different distances away from the posterior side 403. The posterior holes may also be of various sizes and shapes, and may include more or less than two holes. Guide devices of any suitable or effective type may be used to reference one or both of anterior or posterior portions of a femur to correspondingly align the fasteners. In the illustrated embodiment, the posterior holes 441 and the anterior holes 442 are standard round holes that extend completely through the body 401. In other embodiments, the holes may be of any other suitable or effective shape and size, and may extend only partially through a body.

The cutting block 400 may include several additional fastener holes 443, 444, 445 in the body 401 sized and configured to receive one or more fasteners to secure the cutting block 400 to the femur 1000 while one or more cuts are made through one or more of the slots 450, 451, 453, 454. The additional fastener holes 443, 444, 445 may be intermittently or provisionally used to couple the cutting block 400 to the femur 1000 at various times during procedures performed with the cutting block 400. For example, fasteners may be removed from select holes when the fasteners would otherwise interfere with a cutting instrument during a particular step of a procedure, but positioned through select holes at another step of a procedure. Any or all fasteners referred to herein in the various embodiments may include but are not limited to pins, screws, dowels, rods, spikes, or any other suitable or effective mechanism that may be attached or anchored to bone. Such fasteners may be configured with or without heads or similar mechanisms that may be used to hold a cutting block against a femur.

A kit of cutting blocks, or in some embodiments a portion of a kit of cutting blocks, is illustrated in FIG. 11. FIG. 11 illustrates several cutting blocks 200, 300 and 400. The cutting block 400 is a first cutting block of the kit, and has been described in detail above. A second cutting block 200 of a smaller size than the cutting block 400 is shown at two locations in FIG. 11. As used herein, a designation that the second cutting block 200 is of a smaller size may mean that the second cutting block 200 may itself be smaller than the cutting block 400 and/or that the second cutting block 200 is designed to provide preparation of the femur 1000 for a femoral component that is smaller than the femoral component for which the cutting block 400 is used to prepare the femur 1000.

In the illustrated embodiment, the second cutting block 200 is a modification of a standard 4-in-1 cutting block similar to the cutting block 400, and also includes slots for cutting anterior, posterior, and two chamfered cuts, as are well-known in the art. Other embodiments of a second cutting block may include more or fewer slots or other mechanisms for directing the cutting or shaping of a femur.

The second cutting block 200 may include two posterior holes 241 and two anterior holes 242, as partially illustrated in FIG. 11, and are sized and configure similar to the anterior and posterior holes of the cutting block 400. The two anterior holes 242 are positioned in the anterior half of a body 201 of the second cutting block 200, and are also configured to align with one or more fasteners placed in the femur 1000 after being aligned by a guide used to reference an anterior portion of the femur 1000. The two anterior holes 242 are each positioned substantially the same anterior-to-posterior distance away from an anterior side 202 of the body 201. In other embodiments, the anterior holes 242 may be positioned different distances away from the anterior side 202. The anterior holes may also be of various sizes and shapes, and may include more or less than two holes. The second cutting block 200 may also include posterior holes 241 in the posterior half of the body 201 that are configured to align with fasteners that have been placed in the femur 1000 after being aligned by a guide used to reference a posterior portion of the femur 1000. The two posterior holes 241 are each positioned substantially the same anterior-to-posterior distance away from a posterior side 203 of the body 201. In other embodiments, the posterior holes 241 may be positioned different distances away from the posterior side 203. The posterior holes may also be of various sizes and shapes, and may include more or less than two holes. Guide devices of any suitable or effective type may be used to reference one or both of anterior or posterior portions of a femur to align the fasteners. The posterior holes 241 and the anterior holes 242 may be configured as standard round holes that extend completely through the body 201. In other embodiments, holes may be of any other suitable or effective shape and size, and may extend partially through the body.

The anterior holes 242 of the second cutting block 200 may be positioned substantially the same anterior-to-posterior distance from the anterior side 202 of the second cutting block 200 as the anterior holes 442 of the cutting block 400 are positioned from the anterior side 402 of the cutting block 400. Additionally, in the illustrated embodiment, the posterior holes 241 of the second cutting block 200 are positioned substantially the same anterior-to-posterior distance from the posterior side 203 of the second cutting block 200 as the posterior holes 441 of the cutting block 400 are from the posterior side 403 of the cutting block 400. This arrangement of anterior and posterior holes is useful in reducing the number of cutting blocks required to accomplish a full range of femoral preparations or procedures. For example, and only considering the cutting block 400 and the second cutting blocks 200 illustrated in FIG. 11, because the second cutting blocks 200 are configured to either be aligned by the anterior holes 242, which are a result of an anterior referencing technique, or by the posterior holes 241, which are results of a posterior referencing technique, rather than needing three cutting blocks to downsize from the cutting block 400 to the next smaller size with both an anterior referencing technique and a posterior referencing technique, only two cutting blocks are required. Specifically, if a downsizing is needed and an anterior referencing technique is selected, the cutting block 400 can be removed from fasteners that match the anterior holes 442, and the second cutting block 200 can be placed over the fasteners through the anterior holes 242. If a downsizing is needed and a posterior referencing technique is selected, the cutting block 400 can be removed from fasteners that match the posterior holes 441, and the second cutting block 200 can be placed over the fasteners through the posterior holes 241.

The second cutting block 200 may include several additional fastener holes 243, 244 (and others not shown) positioned in the body 201 and configured to receive one or more fasteners to secure the second cutting block 200 to the femur 1000 while one or more cuts are made through one or more of the slots. The additional fastener holes may be used intermittently or provisionally to couple the second cutting block 200 to the femur 1000 at various times during procedures performed with the second cutting block 200, as described in association with the cutting block 400. Any or all fasteners referred to herein in the various embodiments may include but are not limited to pins, screws, dowels, rods, spikes, or any other suitable or effective mechanism that may be attached or anchored to bone. Such fasteners may be configured with or without heads or similar mechanisms that may be used to hold a cutting block against a femur.

The third cutting block 300 illustrated in FIG. 11 is a modification of a standard 4-in-1 cutting block similar to the cutting block 400, and also includes slots for cutting anterior, posterior, and two chamfered cuts, as are well-known in the art. Other embodiments of a third cutting block of the invention may include more or fewer slots or other mechanisms for directing the cutting or shaping of a femur. The third cutting block 300 is of a smaller size than the cutting block 400 or the second cutting block 200. As used herein, a designation that the third cutting block 300 is of a smaller size may mean that the third cutting block 300 may itself be smaller than the cutting blocks 200, 400 and for that the third cutting block 300 is designed to provide preparation of the femur 1000 for a femoral component that is smaller than the femoral component for which the cutting blocks 200, 400 are used to prepare the femur 1000.

The third cutting block 300 illustrated in FIG. 11 includes two posterior holes 341 and two anterior holes 342, as partially illustrated in FIG. 11, and are sized and configured. similar to the anterior and posterior holes of the cutting block 400. The two anterior holes 342 are positioned in the anterior half of the body 301 of the third cutting block 300 and are sized and configured to align with one or more fasteners placed in the femur 1000 after being aligned by a guide used to reference an anterior portion of the femur 1000. The two anterior holes 342 are each positioned substantially the same anterior-to-posterior distance away from an anterior side 302 of the body 301. In other embodiments, the anterior holes 342 may be positioned different distances away from the anterior side 302. The anterior holes may also be of various sizes and shapes, and may include more or less than two holes. The third cutting block 300 may also include posterior holes 341 in the posterior half of the body 301 that are configured to align with fasteners that have been placed in the femur 1000 after being aligned by a guide used to reference a posterior portion of the femur 1000. The two posterior holes 341 are each positioned substantially the same anterior-to-posterior distance away from a posterior side 303 of the body 301. In other embodiments, the posterior holes 341 may be positioned different distances away from the posterior side 303. The posterior holes may also be of various sizes and shapes, and may include more or less than two holes. Guide devices of any suitable or effective type may be used to reference one or both of anterior or posterior portions of a femur to align fasteners.

The posterior holes 341 and the anterior holes 342 may each be configured as standard round holes that extend completely through the body 301. In other embodiments, holes may be of any other suitable or effective shape and size, and may extend partially through the body.

The anterior holes 342 of the third cutting block 300 are positioned substantially the same anterior-to-posterior distance from the anterior side 302 of the third cutting block 300 as the anterior holes 442 of the cutting block 400 are from the anterior side 402 of the cutting block 400. Additionally, in the illustrated embodiment the posterior holes 341 of the third cutting block 300 are positioned substantially the same anterior-to-posterior distance from the posterior side 303 of the third cutting block 300 as the posterior holes 441 of the cutting block 400 are from the posterior side 403 of the cutting block 400. This arrangement of anterior and posterior holes is useful in reducing the number of cutting blocks required to accomplish a full range of femoral preparations or procedures. For example, and considering cutting block 400, the second cutting blocks 200 and the third cutting blocks 300 illustrated in FIG. 11, because the second cutting block 200 and a third cutting block 300 are configured to either be aligned by their anterior holes 242, 342, which are a result of an anterior referencing technique, or are configured to be aligned by their posterior holes 241, 341, which are results of a posterior referencing technique, rather than needing five cutting blocks to downsize one or two times from the cutting block 400 to the next smaller sizes with both an anterior referencing technique in a posterior referencing technique, only three cutting blocks are required. Specifically, if a downsizing is needed and an anterior referencing technique is selected, the cutting block 400 can be removed from fasteners that match the anterior holes 442, and the second cutting block 200 can be placed over the fasteners through its anterior holes 242, or the third cutting block 300 can be placed over the fasteners through its anterior holes 342. If a downsizing is needed and a posterior referencing technique is selected, the cutting block 400 can be removed from fasteners that match the posterior holes 441, and the second cutting block 200 can be placed over the fasteners through its posterior holes 241, or the third cutting block 300 can be placed over the fasteners through its posterior holes 341.

The third cutting block 300 may include several additional fastener holes 344 (and others not shown) in the body 301 which are sized and configured to receive one or more fasteners to secure the third cutting block 300 to the femur 1000 while one or more cuts are made through one or more of the slots. The additional fastener holes may be intermittently or provisionally used to couple the third cutting block 300 to the femur 1000 at various times during procedures performed with the third cutting block 300, as described above in association with the cutting block 400. Any or all fasteners referred to herein in various embodiments may include but are not limited to pins, screws, dowels, rods, spikes, or any other suitable or effective mechanism that may be attached or anchored to bone. Such fasteners may be configured with or without heads or similar mechanisms that may be used to hold a cutting block against a femur.

Kit embodiments of the invention may include any number of additional sizes of cutting blocks and other instrumentation such as but not limited to, guides, fasteners, and cutting instruments. Some or all of the additional cutting blocks may include mechanisms for providing posterior and anterior referencing by the cutting blocks.

Embodiments of the invention may include methods of implanting a knee arthroplasty femoral component. A first cutting block, such as the cutting block 400, may be provided as an act or step of some method embodiments. Such method embodiments may utilize the cutting block 400 and variations to the cutting block 400 described herein, or other cutting blocks compatible with the methods described herein. A second cutting block of a size smaller than the size of the first cutting block may be provided as an act or step of some method embodiments. The second, smaller cutting block may be the same as the second cutting block 200 or the third cutting block 300 and variations described herein, or may be a cutting block compatible with the methods described herein. The second, smaller cutting block of some embodiments is configured to either be aligned with an anterior reference to the femur or a posterior reference to the femur. Method embodiments may include providing as second cutting block with one or more anterior holes that are positioned substantially the same anterior-to-posterior distance from the anterior side of the second cutting block as one or more anterior holes of the first cutting block are from the anterior side of the first cutting block. For example, the second cutting block 200 has two anterior holes 242 that are positioned substantially the same anterior-to-posterior distance from the anterior side 202 of the second cutting block 200 as the anterior holes 442 of the cutting block 400 are from the anterior side 402 of the first cutting block 400. In some embodiments, the second cutting block includes one or more posterior holes that are positioned substantially the same anterior-to-posterior distance from the posterior side of the second cutting block as one or more posterior holes of the first cutting block are from the posterior side of the first cutting block. For example, the second cutting block 200 includes two posterior holes 241 that are positioned substantially the same anterior-to-posterior distance from the posterior side 203 of the second cutting block 200 as the two posterior holes 441 of the cutting block 400 are from the posterior side 403 of the cutting block 400.

An act or step of some methods may include choosing to change the size of a femoral component, and consequently the cutting block, intraoperatively. In some circumstances, a larger size may be chosen, and in other circumstances a smaller size may be chosen. If an anterior referencing technique is being followed, choosing a smaller size results in more bone resection from the posterior condyles, which may in turn increase the flexion space, but anterior femoral notching is avoided. When following a posterior referencing technique, selection of a larger size may increase the chance of overstuffing the patellofemoral joint. Changing between a posterior referencing technique and an anterior referencing technique intraoperatively may give a surgeon the opportunity to select alignments and conditions the surgeon believes are most beneficial to the patient.

In one exemplary circumstance, when a choice is made to downsize from a first cutting block (such as the cutting block 400) to a second, smaller cutting block (such as the second cutting block 200) intraoperatively, it may be advantageous to change between an anterior referencing technique and a posterior referencing technique. For example, if a surgeon believes it is particularly important to avoid anterior notching for a specific patient and a posterior referencing technique is being followed, the surgeon could choose to both downsize and switch from a posterior referencing technique to an anterior referencing technique under embodiments of the invention described herein. Furthermore, in some embodiments of the present invention, the second, smaller cutting block described herein could be used for either continuing to follow a posterior referencing technique, or switching to an anterior referencing technique.

By way of more specific example, if the cutting block 400 were being used to perform a posterior referencing technique and a surgeon determined that a smaller size implant, and therefore a smaller cutting block, is needed, the surgeon could select the second cutting block 200 intraoperatively. If the surgeon wanted to continue performing a posterior referencing technique, then the cutting block 400 could be removed from fasteners that had previously been inserted through the posterior holes 441. The second cutting block 200 could then be placed over the fasteners into the posterior holes 241. In this manner, the posterior referencing technique may continue to be followed. However, if the choice was made to switch to an anterior referencing technique, the same second cutting block 200 could be used. In particular, the cutting block 200 could be used with fasteners that were placed in the femur 1000 by coupling the second cutting block 200 over the fasteners and into the anterior holes 242. Note that fasteners for use within an anterior referencing technique may be aligned and placed in the femur 1000 with a guide or any other effective method to properly reference and position the second cutting guide 200 relative to an anterior cortex of the femur 1000.

Once the second cutting block is aligned, an act or step of some methods includes cutting the femur as guided by the cutting block. For example, with the second cutting block 200 aligned on the resected femur 1000, cutting tools may be inserted through the slots in the second cutting block 200 to guide cutting of the resected femur 1000. Similar cutting may be accomplished through any other suitable or effective cutting block. The third cutting block 300 describe herein, for example, could be used as a downsize from either the cutting block 400 or the second cutting block 200 in some embodiments.

An act or step of some method embodiments includes implanting the knee arthroplasty femoral component. The knee arthroplasty femoral component may be a total knee arthroplasty component, or a component for a partial knee arthroplasty. Other acts or steps such as, without limitation, inserting and testing trials, accomplishing soft tissue releases, and/or applying adhesives and fasteners may be performed in addition to the particular acts or steps described herein.

Various embodiments of an instrument set in whole or its components individually may be made from any suitable biocompatible material. For example and without limitation, biocompatible materials may include, in whole or in part, non-reinforced polymers, reinforced polymers, metals, ceramics, adhesives, reinforced adhesives, and any combination of these materials. Reinforcing of polymers may be accomplished with carbon, metal, or glass or any other suitable or effective material. Examples of biocompatible polymer materials include polyamide base resins, polyethylene, low density polyethylene, polymethylmethacrylate (PMMA), polyetheretherketone (PEEK), polyetherketoneketone (PEKK), a polymeric hydroxyethylmethaerylate (PHEMA), and polyurethane, any of which may be reinforced. Example biocompatible metals include stainless steel and other steel alloys, cobalt chrome alloys, zirconium, oxidized zirconium, tantalum, titanium, titanium alloys, titanium-nickel alloys such as Nitinol, and other superelastic or shape-memory metal alloys.

Terms such as anterior, posterior, medial, lateral, over, and the like have been used relatively herein. However, such terms are not limited to specific coordinate orientations, distances, or sizes, but are used to describe relative positions referencing particular embodiments. Such terms are not generally limiting to the scope of the claims made herein.

Any embodiment or feature of any section, portion, or any other component shown or particularly described in relation to various embodiments of similar sections, portions, or components herein may be interchangeably applied to any other similar embodiment or feature shown or described herein.

While embodiments of the invention have been illustrated and described in detail in the disclosure, the disclosure is to be considered as illustrative and not restrictive in character. All changes and modifications that come within the spirit of the invention are to be considered within the scope of the disclosure.

What is claimed is:

1. A femoral sizing guide, comprising:
   a base including a main body and one or more paddles that extend from the main body, wherein the one or more paddles are configured to contact posterior condyles of a patient;
   a posterior reference frame pivotally coupled with the base, wherein the posterior reference frame includes one or more holes for receiving one or more fasteners;
   an anterior reference frame slidably coupled to the posterior reference frame; and
   a stylus coupled to the anterior reference frame, wherein the stylus extends away from the plane in which the anterior reference frame slides relative to the posterior reference frame;
   wherein a pivot between the base and the posterior reference frame is positioned in an anterior half of the posterior reference frame.

2. The femoral sizing guide of claim 1 wherein the base includes one or more holes for receiving one or more fasteners.

3. The femoral sizing guide of claim 1 wherein the pivot between the base and the posterior reference frame is positioned in an anterior third of the posterior reference frame.

4. The femoral sizing guide of claim 1 wherein the pivot between the base and the posterior reference frame is positioned in an anterior quarter of the posterior reference frame.

5. The femoral sizing guide of claim 1 further comprising a posterior lock configured to restrict pivoting of the posterior reference frame relative to the base.

6. The femoral sizing guide of claim 1 wherein the one or more holes in the posterior reference frame are not sized and configured to receive an intramedullary rod.

7. The femoral sizing guide of claim 1 wherein the base includes an indicator configured to be read relative to the indicator's position on a scale on the posterior reference frame.

8. The femoral sizing guide of claim 1 wherein the posterior reference frame includes an indicator configured to be read relative to the indicator's position on a scale on the base.

9. The femoral sizing guide of claim 1 wherein the anterior reference frame includes one or more holes for receiving one or more fasteners.

10. The femoral sizing guide of claim 1 further comprising an anterior lock configured to restrict sliding of the anterior reference frame relative to the posterior reference frame.

11. A femoral sizing guide, comprising:
    a base including a main body and one or more paddles that extend from the main body, wherein the one or more paddles are configured to contact posterior condyles of a patient;

a posterior reference frame pivotally coupled with the base, wherein the posterior reference frame includes one or more holes for receiving one or more fasteners;
an anterior reference frame slidably coupled to the posterior reference frame; and
a stylus coupled to the anterior reference frame, wherein the stylus extends away from the plane in which the anterior reference frame slides relative to the posterior reference frame; and
wherein in addition to the one or more holes for receiving one or more fasteners in the posterior reference frame, the anterior reference frame includes one or more holes for receiving one or more fasteners, and the one or more holes in the posterior reference frame are different from the one or more holes in the anterior reference frame such that an instrument configured to couple with fasteners aligned for use with the posterior reference frame will not couple with fasteners aligned for use with the anterior reference frame.

12. A method of preparing a femur to receive a femoral component of a knee arthroplasty system, the method comprising:
making a distal cut across the femur;
placing a femoral sizing guide against the distal cut, the femoral sizing guide comprising:
a base including a main body and one or more paddles that extend from the main body, wherein the one or more paddles are configured to contact posterior condyles of the femur,
a posterior reference frame coupled with the base,
an anterior reference frame slidably coupled to the posterior reference frame, and
a stylus coupled to the anterior reference frame, wherein the stylus extends away from the plane in which the anterior reference frame slides relative to the posterior reference frame;
seating the one or more paddles against the posterior condyles of the femur;
sliding the anterior reference frame relative to the posterior reference frame and adjusting the stylus to contact the lateral anterior cortex of the femur;
determining a size of femoral component to implant based on indications displayed on the femoral sizing guide;
providing an option to place fasteners through one or more holes in the posterior reference frame and/or through one or more holes in the anterior reference frame, wherein placing fasteners through one or more holes in the posterior reference frame facilitates a posterior referencing technique, and wherein placing fasteners through one or more holes in the anterior reference frame facilitates an anterior referencing technique; and
removing the femoral sizing guide from the femur and coupling a cutting block to the femur via alignment with one or more of the fasteners.

13. The method of claim 12 wherein the placing a femoral sizing guide against the distal cut includes placing a posterior reference frame pivotally coupled with the base against the distal cut.

14. The method of claim 13 further comprising:
pivoting the posterior reference frame relative to the base such that a line substantially perpendicular to an anterior-to-posterior dimension of the posterior reference frame is aligned with an epicondylar axis of the femur while the one or more paddles are in contact with the posterior condyles of the femur; and
activating a posterior lock to restrict pivoting of the posterior reference frame relative to the base.

15. The method of claim 12 further comprising coupling the base to the femur with one or more fasteners.

16. The method of claim 12 further comprising placing fasteners through the one or more holes in the posterior reference frame while performing a posterior referencing technique.

17. The method of claim 12 further comprising placing fasteners through the one or more holes in the anterior reference frame while performing an anterior referencing technique.

18. The method of claim 12 further comprising placing fasteners through the one or more holes in the posterior reference frame and placing fasteners through the one or more holes in the anterior reference frame.

19. A method of preparing a femur to receive a femoral component of a knee arthroplasty system, the method comprising:
making a distal cut across the femur;
placing a femoral sizing guide against the distal cut, the femoral sizing guide comprising:
a base including a main body and one or more paddles extending from the main body, wherein the one or more paddles are configured to contact posterior condyles of the femur,
a posterior reference frame coupled with the base,
an anterior reference frame slidably coupled to the posterior reference frame, and
a stylus coupled to the anterior reference frame, wherein the stylus extends away from a plane in which the anterior reference frame slides relative to the posterior reference frame;
seating the one or more paddles against the posterior condyles of the femur;
sliding the anterior reference frame relative to the posterior reference frame and adjusting the stylus to contact a lateral anterior cortex of the femur;
determining a size of femoral component to implant based on indications displayed on the femoral sizing guide;
providing an option to place fasteners through one or more holes in the posterior reference frame and/or through one or more holes in the anterior reference frame, wherein placing fasteners through one or more holes in the posterior reference frame facilitates a posterior referencing technique, and wherein placing fasteners through one or more holes in the anterior reference frame facilitates an anterior referencing technique;
placing fasteners through the one or more holes in the posterior reference frame while performing a posterior referencing technique;
selecting a femoral component of a smaller size than initially determined;
changing to an anterior referencing technique;
placing fasteners through the one or more holes in the anterior reference frame; and
removing the femoral sizing guide from the femur and coupling an anterior referencing cutting block to the femur with one or more of the fasteners placed through the one or more holes in the anterior reference frame.

20. The method of claim 19 wherein the placing a femoral sizing guide against the distal cut includes placing a posterior reference frame pivotally coupled with the base against the distal cut.

21. The method of claim 20 further comprising:
pivoting the posterior reference frame relative to the base such that a line substantially perpendicular to be anterior to posterior dimension of the posterior reference frame is aligned with an epicondylar axis of the femur while the one or more paddles are in contact with the posterior condyles of the femur; and
activating a posterior lock to restrict pivoting of the posterior reference frame relative to the base.

22. The method of claim 19 further comprising coupling the base to the femur with one or more fasteners.

23. A kit including the femoral sizing guide of claim 12, the kit further including a cutting block, the cutting block comprising:
a body including two or more slots configured to receive and direct a cutting instrument used to prepare a distal femur to receive a femoral component of a knee arthroplasty system;
one or more anterior holes in an anterior half of the body configured to align with one or more fasteners placed in the femur after being aligned by the one or more holes of the anterior reference frame; and
one or more posterior holes in a posterior half of the body that are configured to align with one or more fasteners placed in the femur after being aligned by the one or more holes of the posterior reference frame; and
wherein the one or more anterior holes are different from the one or more posterior holes such that the posterior holes will not couple with the fasteners aligned for use with the anterior reference frame.

24. The kit of claim 23 wherein the body includes four of the slots configured to receive and direct a cutting instrument.

25. The kit of claim 24 wherein the four slots include an anterior slot, a posterior slot, and two intersecting slots positioned between the anterior slot and the posterior slot.

26. The kit of claim 23 wherein the anterior holes are each positioned substantially the same anterior-to-posterior distance away from an anterior side of the body.

27. The kit of claim 23 wherein the posterior holes are each positioned substantially the same anterior-to-posterior distance away from a posterior side of the body.

28. The kit of claim 23 further comprising one or more additional holes in the body configured to receive one or more fasteners to secure the cutting block to the femur while one or more cuts are made through one or more of the slots.

* * * * *